US006660868B2

(12) United States Patent
Irie

(10) Patent No.: US 6,660,868 B2
(45) Date of Patent: Dec. 9, 2003

(54) PHOTO-INDUCED PHASE TRANSITION ORGANIC MATERIAL

(75) Inventor: Masahiro Irie, Fukuoka (JP)

(73) Assignee: Japan Science and Technology Corporation, Kawacuchi (JP)

( * ) Notice: Subject to any disclaimer, the term of this patent is extended or adjusted under 35 U.S.C. 154(b) by 0 days.

(21) Appl. No.: 09/927,931

(22) Filed: Aug. 13, 2001

(65) Prior Publication Data
US 2002/0007072 A1 Jan. 17, 2002

Related U.S. Application Data

(63) Continuation of application No. PCT/JP00/01330, filed on Mar. 6, 2000.

(51) Int. Cl.[7] .............................................. C07D 31/56
(52) U.S. Cl. ...................................... 548/146; 549/146
(58) Field of Search ............................ 549/29, 41, 49, 549/61

(56) References Cited

FOREIGN PATENT DOCUMENTS

| JP | 8-119963 | 5/1996 |
|----|----------|--------|
| JP | 9-241625 | 9/1997 |
| JP | 10-251630 | 9/1998 |
| JP | 11-255764 | 9/1999 |
| JP | 11-311813 | 11/1999 |
| JP | 2000-47270 | 2/2000 |
| JP | 2000-87024 | 3/2000 |

OTHER PUBLICATIONS

Irie, Masahiro (DN 132:243738, CAPLUS, abstract of JP 2000087024).*
Irie, Masahiro (DN 127:197611, HCAPLUS, abstract of Mol. Cryst. Liq. Cryst. Sci. Tech., Sect. A (1997), 297, 81–84).*
Irie, Masahiro (DN 132:243738, CAPLUS, abstract of 2000087024).*
Picosecond Laser Photolysis Studies on a Photochromic Dithenylethene in Solution and in Crystalline Phases, Chemical Physics Letters, 1997, vol. 269, No. 314, pp. 281–285.

* cited by examiner

Primary Examiner—Sabiha Qazi
(74) Attorney, Agent, or Firm—Kanesaka & Takeuchi

(57) ABSTRACT

A photo-induced phase transition organic material is composed of a diheteroarylethene-based compound within which the photo-chromic reaction occurs in the crystalline state. The diheteroarylethene-based compound of the present invention reversibly changes in color with light irradiation and also changes in phase from the open-ring form in the crystalline state to the closed-ring form in the crystalline state, or from the closed-ring form in the crystalline state to the open-ring form in the crystalline state via the liquid state, and can be applicable to optical recording media, display panels, sensors, optical switch devices and the like, by taking advantages of its variations in color with light irradiation and also its changes in physical property, such as the refractive index and the permeability, with its changes in phase.

5 Claims, 1 Drawing Sheet open-ring form    transition ratio    closed-ring form open-ring form    mixing ratio    closed-ring form

PHOTO-INDUCED PHASE TRANSITION ORGANIC MATERIAL

CROSS REFERENCE TO RELATED APPLICATION

This is a continuation application of PCT/JP00/01330 filed on Mar. 6, 2000.

FIELD OF THE INVENTION

The present invention relates to a photo-induced phase transition organic material, more particularly to a photo-induced phase transition organic material composed of a diheteroarylethene-based compound in which the phase transition occurs in response to light irradiation in a crystalline state, especially even in a single-crystalline state.

BACKGROUND OF THE INVENTION

A photochromic material, which means the material containing a sort of molecule or molecular assembly from which two isomers having different colors are reversibly formed due to the action of light, has been expected as a photofunctional material since a variety of its physical properties, such as not only the color, but also the dielectric constant, the oxidation/reduction potential, etc., reversibly varies with light irradiation in connection with its photo-chromic reaction. Both photochromic molecules and molecular assemblies conventionally employed are to be transferred with light irradiation from colorless state to one-colored state in a solution or a macromolecular medium, such as red and blue, while method of applying various chemical modifications to the photochromic molecules have been studied in order to obtain the photochromic material which can develop various colors.

OBJECT AND SUMMARY OF THE INVENTION

The present invention has arisen from the detailed analysis of the mechanism of the photochromic reaction of diheteroarylethene-based compound which does not need any dispersion medium, and the object of the present invention is to provide a photo-induced phase transition organic material which utilizes the photochromic reaction of diheteroarylethene-based compound.

The photo-induced phase transition organic material of the present invention is composed of a diheteroarylethene-based compound within which the photochromic reaction occurs in the crystalline state, especially in the single-crystalline state.

On the other hand, conventional photochromic compound undergoes the photochromic reaction in a state where they are dispersed or dissolved in a macromolecular-film or a solvent, and there has been no photochromic compound which stably undergoes the photochromic reaction in a crystalline phase like the photochromic material of the present invention.

BRIEF DESCRIPTION OF THE DRAWINGS

FIG. 1a is a phase diagram in case of light irradiation and FIG. 1b is a phase diagram in case of a mixture.

DETAILED DESCRIPTION OF THE PREFERRED EMBODIMENTS

Figure 1A:
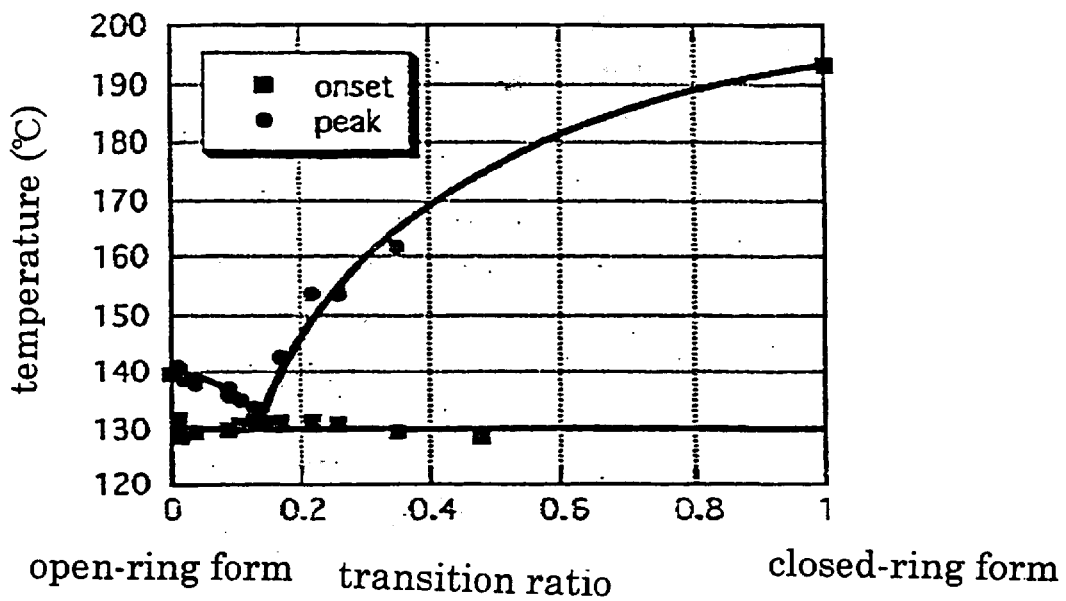
FIGS. 1a and 1b are phase diagrams illustrating the relationship between the open-ring form/ring-closure form rate of a compound (II) to be obtained in the following Example of Synthesis 1 and its melting point, where

Hereinafter, embodiments of the present invention will be described in detail.

An example of the diheteroarylethene-based compound of the present invention is the one expressed by the following general formula [1]:

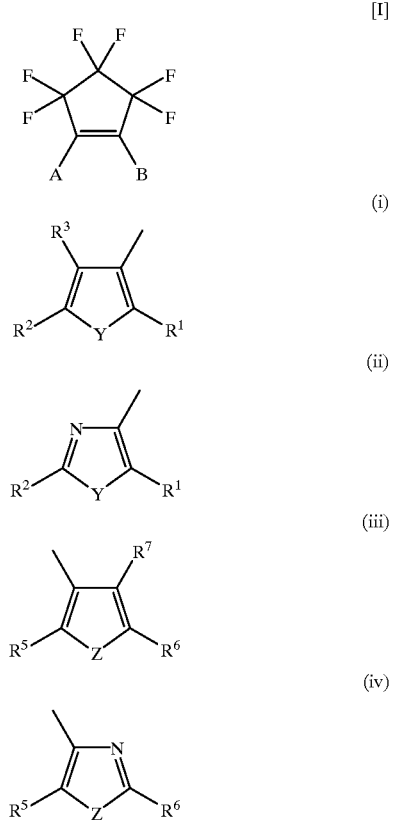

In the general formula [I], "A" expresses a substituent (i) or (ii). In the substituents (i) and (ii), "$R^1$" expresses an alkyl group, an alkoxyl group, a halogen atom, a trifluoromethyl group, a cyano group, or an aryl group which may have at least one substituent. "$R^2$" and "$R^3$" express a hydrogen atom, an alkyl group, an alkoxyl group, a halogen atom, a trifluoromethyl group, a cyano group, an aryl group which may have at least one substituent, respectively, wherein "$R^2$" and "$R^3$" are independent of each other. Alternatively, "$R^2$" and "$R^3$" may be bonded to each other to form a carbocyclic ring which may have at least one substituent, or a heterocyclic ring which may have at least one substituent. "Y" expresses —O—, —S—, or —NR$^4$— in which "$R^4$" expresses a hydrogen atom, an alkyl group which may have at least one substituent, an aryl group which may have at least one substituent, or a cycloalkyl group which may have at least one substituent. "B" expresses a substituent (iii) or (iv). In the substituents (iii) and (iv), "$R^5$" expresses an alkyl group, an alkoxyl group, a halogen atom, or a trifluoromethyl group. "$R^6$" and "$R^7$" express a hydrogen atom, an alkyl group, an alkoxyl group, a halogen atom, a trifluoromethyl group, a cyano group, or an aryl group which may have at least one substituent, respectively, wherein "$R^6$" and "$R^7$" are independent of each other. Alternatively, "$R^6$" and "$R^7$" may be bonded to each other to form a carbocyclic ring which may have at least one substituent, or a heterocyclic ring which may have at least one substituent. "Z" expresses —O—, —S—, or —NR$^4$— in which "$R^4$" expresses a hydrogen atom, an alkyl group which may have at least one substituent, an aryl group which may have at least one substituent, or a cycloalkyl group which may have at least one substituent.

Each of the above compounds transfers in phase from an open-ring form to a closed-ring form with ultraviolet irradiation, while being in the crystalline state.

In the above general formula [I], the following substituents may be employed as substituents A and B, wherein "R" expresses an alkyl group or a phenyl group.

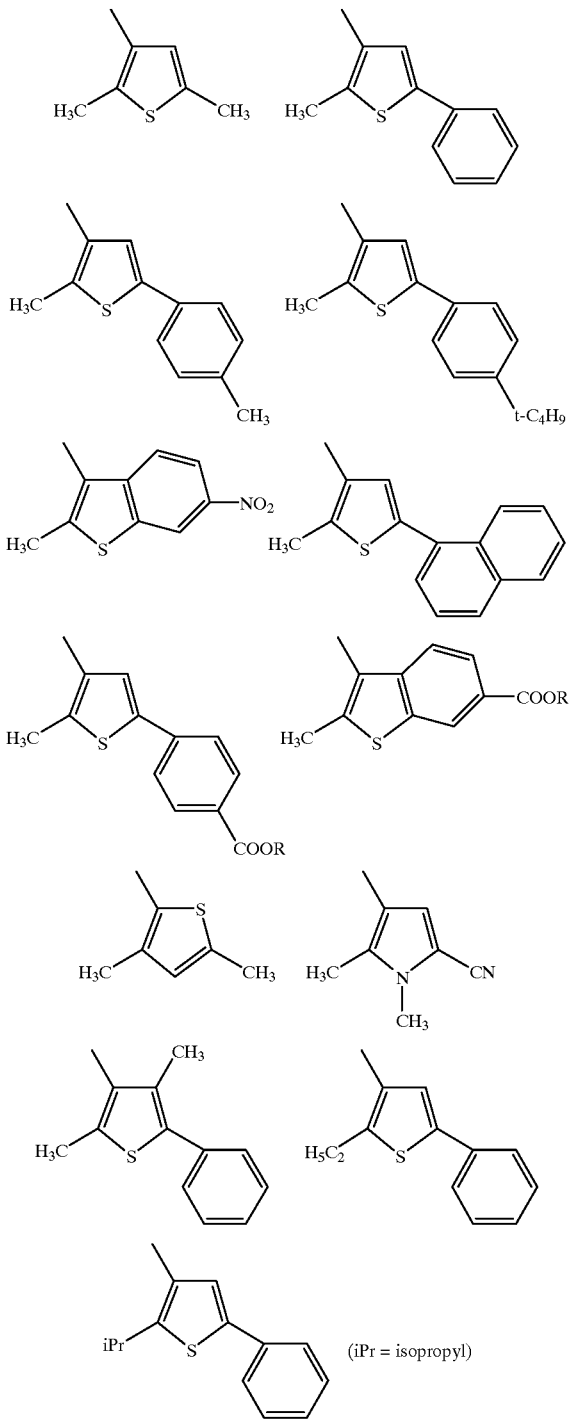

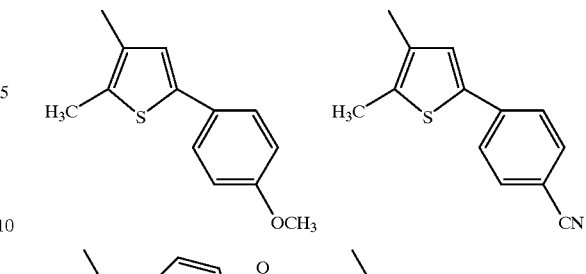

The diheteroarylethene-based compound is 1,2-bis(5-phenyl-2-methylthiophene-3-yl)perfluorocyclopentene as expressed by the following formula [II]: or 1,2-bis(2,5-dimethylthiophene-3-yl)perfluorocyclopentene as expressed by the following formula [III]:

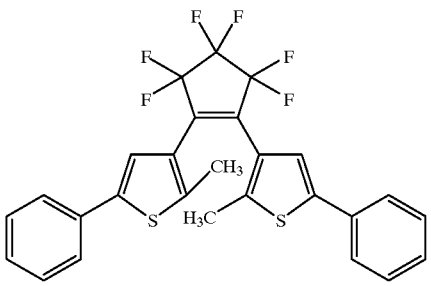

[II]

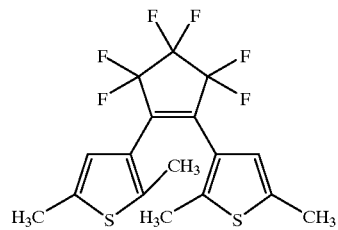

[III]

The diheteroarylethene-based compound is transferred in phase from the open-ring form to the closed-ring form with irradiation of ultraviolet having a wave length of about 300–400 nm, and transferred in phase from the closed-ring form to the open-ring form with visible-light irradiation. The open-ring form differs from the closed-ring form in the melting point thereof.

Hereinafter, the present invention will be described in detail referring to examples of synthesis and examples of practice.

Synthesis Experiment 1
[Synthesis of 3,5-dibromo-2-methylthiophene (II-1)]

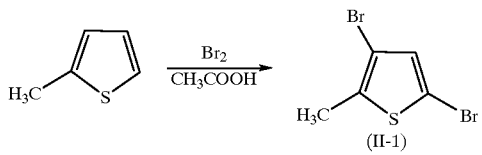

2-methylthiophene of 25.4 g (0.258 mol) and acetic acid of 300 ml were poured into a four-necked flask having a capacity of 1000 ml, and then kept at a temperature of 0° C. with an ice bath. Secondly, bromine of 82.5 g (0.516 mol) was slowly dropped into them with a dropping funnel, and acetic acid of 20 ml was further added into them after the dropping, then the dropping funnel was washed. These ingredients were stirred for 30 minutes, while being kept at a temperature of 0° C. After that, the ice bath was removed and the ingredients were further stirred all night, while being warmed to a room temperature. The solution thus prepared was neutralized with sodium carbonate, added with a solution of sodium thiosulfate to perform ether extraction, washed with brine, and then dried with magnesium sulfate. The magnesium sulfate was removed by filtration after the drying and the ether was distilled off. The remainder was developed with hexane to separate a component of Rf=0.83 by making use of a silica gel chromatographic column. The resultant was distilled under a reduced pressure in order further to separate a component having a boiling point 88 to 90° C. The yield of the compound (II-1) thus obtained was 34.7 g, the rate of the yielding was 52.5%, and the results of NMR analysis were as follows:

$^1$H-NMR (200 MHz, CDCl$_3$, TMS) δ=2.34 (s, 3 H, Me) 6.86 (s, 1 H, aromatic proton)

[Synthesis of 3-bromo 2-methyl-5-thiophene borate (II-2)]

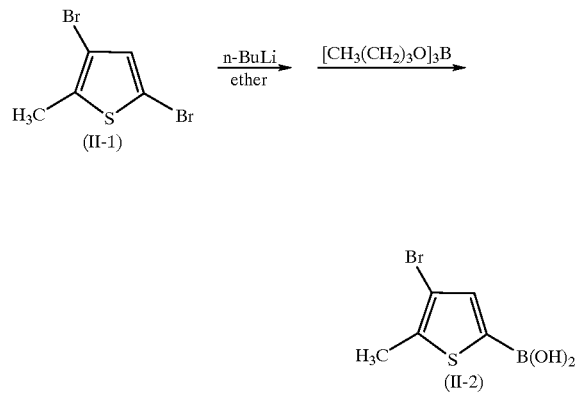

The above compound (II-1) of 34.7 g (0.136 mol) and anhydrous ether of 500 ml were poured in a three-necked flask having a capacity of 2000 ml, and then cooled to −60° C. or less. Secondly, 1.6N n-butyllithium of 87.6 ml was incorporated into these ingredients and stirred for 30 minutes. After addition of 54.6 ml tri-n-butyl borate, the ingredients were kept at a temperature of −60° C. or less for 4 hours, then warmed to a room temperature, stirred for 15 more hours, and further added with water to stop reaction. 1.2N hydrochloric acid was, then, added into the solution thus resulted in order to perform ether extraction. The ether phase thus appeared was further extracted with 1.0N sodium hydroxide solution. After that, the ether was removed, and then concentrated hydrochloric acid was added into the liquid phase until pH of the liquid phase corresponded to 1, while the liquid phase was kept 0° C., in order to separate the crystal. The crystal was filtered out by vacuum filtration and dried under reduced pressure, so that a compound (II-2) was obtained. The yield of the compound (II-2) was 21.6 g, the rate of the yielding was 72.2%, and the results of NMR analysis were as follows:

$^1$H-NMR (200 MHz, CDCl$_3$, TMS) δ=2.46 (s, 3 H, Me) 7.35 (s, 1 H, aromatic proton)

[Synthesis of 3-bromo-2-methyl-5-phenylthiophene (II-3)]

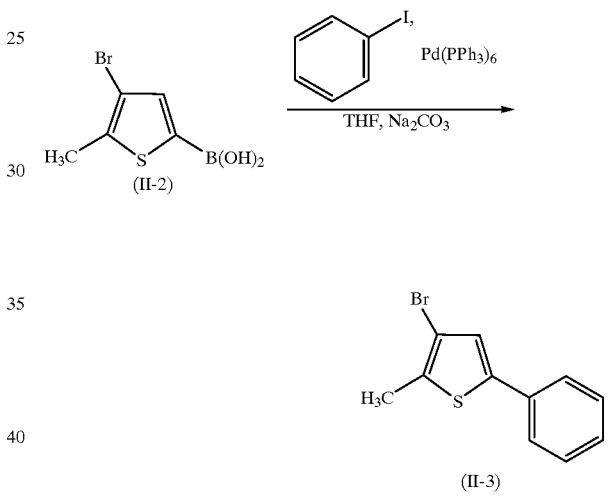

The above compound (II-2) of 10.0 g (45.3 mmol), tetra-hydrofuran of 70 ml, sodium carbonate solution (20% by weight) of 70 ml, iodobenzene of 7.6 ml (68.0 mmol) and tetrakis(triphenyl-phosphine)palladium (0) of 2.36 g were poured in a three-necked flask having a capacity of 500 ml, and then heated under reflux at 70° C. for 2.5 hours in an atmosphere of argon. The solution thus prepared, then, was cooled down to a room temperature, applied with ether extraction, washed with a solution saturated with sodium hydrogen carbonate and water, and further dried with magnesium sulfate. The magnesium sulfate was removed by filtration after the drying and the ether was distilled off. The remainder was developed and separated by hexane by making use of a silica gel chromatographic column, and then recrystallized, so that a compound (II-3) was obtained. The yield of the compound (II-3) was 6.6 g, the rate of the yielding was 57.6%, and the results of NMR analysis were as follows:

$^1$H-NMR (200 MHz, CDCl$_3$, TMS) δ=2.41 (s, 3 H, Me) 7.10 (s, 1 H, aromatic proton) 7.24–7.71 (m 5 H, aromatic proton)

[Synthesis of 1,2-bis(5-phenyl-2-methylthiophene-3-yl) perfluoro-cyclopentene (II)]

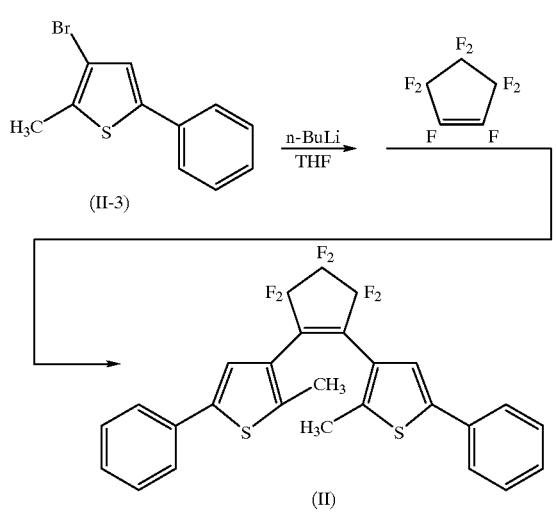

The above compound (II-3) of 6.6 g (26.1 mmol) and tetra-hydrofuran of 200 ml were poured into a three-necked flask having a capacity of 500 ml, and kept at a temperature of 60° C. or less. Secondly, 1.6N n-butyllithium of 17.5 ml (27.4 mmol) was dropped into these ingredients slowly, drop by drop. After that, dropping funnel was washed with tetrahydrofuran of 10 ml, and the solution thus prepared was stirred for 45 minutes. Perfluorocyclopentene of 0.9 ml (11.7 mmol), then, was slowly dropped into the solution, while the solution was kept at a temperature of −60° C. or less. After being stirred for 2 hours, the solution was added with ethanol and water, while being warmed to a room temperature. The solution thus resulted was applied with ether extraction, washed with 1.2N hydrochloric acid and water, and further dried with magnesium sulfate. The magnesium sulfate was removed by filtration after the drying and the ether was distilled off. The remainder was developed and separated by hexane by making use of a silica gel chromatographic column, and then recrystallized, so that a compound (II) composed of colorless cubic crystal was obtained. The yield of the compound (II) was 1.7 g, the rate of the yielding was 31.4%, and the results of analyses about the melting point (m.p.), NMR, IR, molecular weight, etc. were as follows:

m.p.: 139° C.

$^1$H-NMR (200 MHz): δ7.75, 7.30 (m, 10 H, CH of P h), 7.28 (s, 2 H, CH of thiophene), 1.97 (s, 6 H, Me)

$^{13}$C-NMR (50 MHz) δ142.2, 141.1, 133.3, 125.8, 109.8 (8 C, C q) 128.9, 127.8, 125.6 (10 C, C H of Ph), 122.4 (2 C, CH of thiophene), 14.5 (2 C, Me)

MS (m/z): 520 (M$^+$, 64), 505 (100), 490, 472, 385, 121, 77

IR (KBr): 3080, 3020, 2910, 1450, 1340, 1270, 1390, 1340, 1310, 1050, 990, 890, 760, 690 cm$^{-1}$.

anal. Calcd for $C_{27}H_{18}F_6S_2$: C62.30;H3.49

Found: C62.66;H3.72

Synthesis Experiment 2
[Synthesis of 2,5-dimethyl-3-iodothiophene (III-1)]

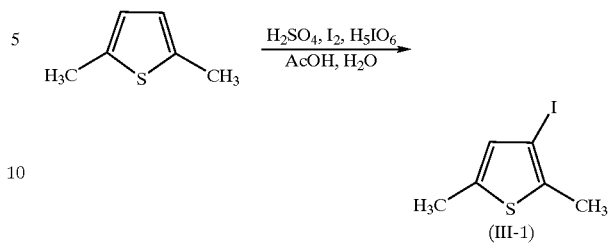

Water of 75 ml, concentrated sulfuric acid of 18 ml, iodine of 11.4 g and iodic acid of 3.5 g were mixed into a solution of 11.2 g 2,5-dimethylthiophene in acetic acid of 100 ml, while the solution was stirred at a room temperature. The mixture was under reflux at 70° C. for 2 hours, and then the reaction mixture was cooled by ice water. The mixture, further, was applied with ether extraction, and its organic layer was washed with water, a solution of sodium carbonate and a solution of sodium thiosulfate, then dried with magnesium sulfate. After that, the solvent was distilled off, and the remainder was developed by hexane by making use of a silica gel chromatographic column to isolate 2,5-dimethyl-3-iodothiophene (III-1). The yield of the compound (III-1) was 16.6 g, the rate of the yielding was 70%, and the results of NMR analysis were as follows:

[Synthesis of 1,2-bis(2,5-dimethylthiophene-3-yl) perfluoro-cyclo-pentene (III)]

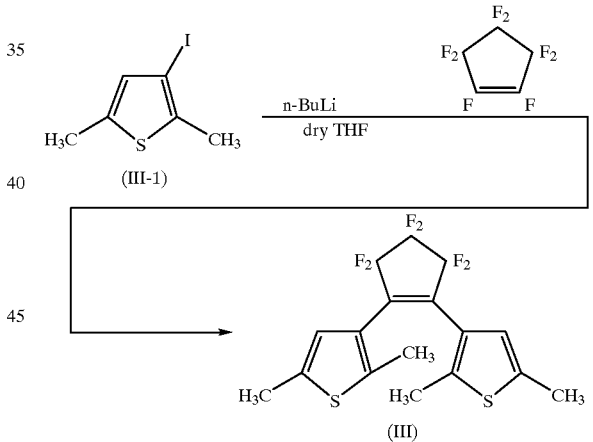

A solution of 1.6N n-butyllithium hexane of 36 ml was dropped into a solution of 12.9 g 2,5-dimethyl-3-iodothiophene (III-1) in xerotetrahydrofuran of 70 ml, while the solution was cooled at 70° C. by dry ice-methanol bath in an atmosphere of argon, the solution was stirred for one hour, and then 2.5 ml perfluorocyclopentene was dropped into the solution in three steps at intervals of 30 minutes. After being cooled with water, the mixed solution was warmed to a room temperature, and then the solvent was distilled off. The mixture, further, was extracted by ether, washed with brine, and then dried with magnesium sulfate. After that, the solvent was distilled off, and the remainder was developed by hexane by making use of a silica gel chromatographic column and recrystallized to isolate 1,2-bis(2,5-dimethyl-thiophene-3-yl)perfluorocyclopentene (III). The yield of the compound (III) was 6.94 g, the rate of the yielding was 65%, and the results of NMR analysis were as follows:

$^1$H NMR (200 MHz, CDCl$_3$, TMS) δ=1.81 (6 H, s, Me) 2.41 (6 H, s, Me) 6.72 (2 H, s, aromatic H)

EXAMPLE 1

The single crystal (II-A) of the compound (II) was obtained from a solution of the compound (II) in hexane by the solvent evaporation method. The single crystal (II-A) was transparent and colorless. On the other hand, the closed-ring forms of the compound (II-A) were formed by irradiating the above hexane solution with ultraviolet rays having a wavelength of 350 to 400 nm, and, among the resulted closed-ring forms, only the blue one was extracted by the column chromatography. The extracted closed-ring form was dissolved into the hexane solution again, and then the closed-ring single crystal (II-B) was obtained from this solution by the solvent evaporation method.

Figure 1B:
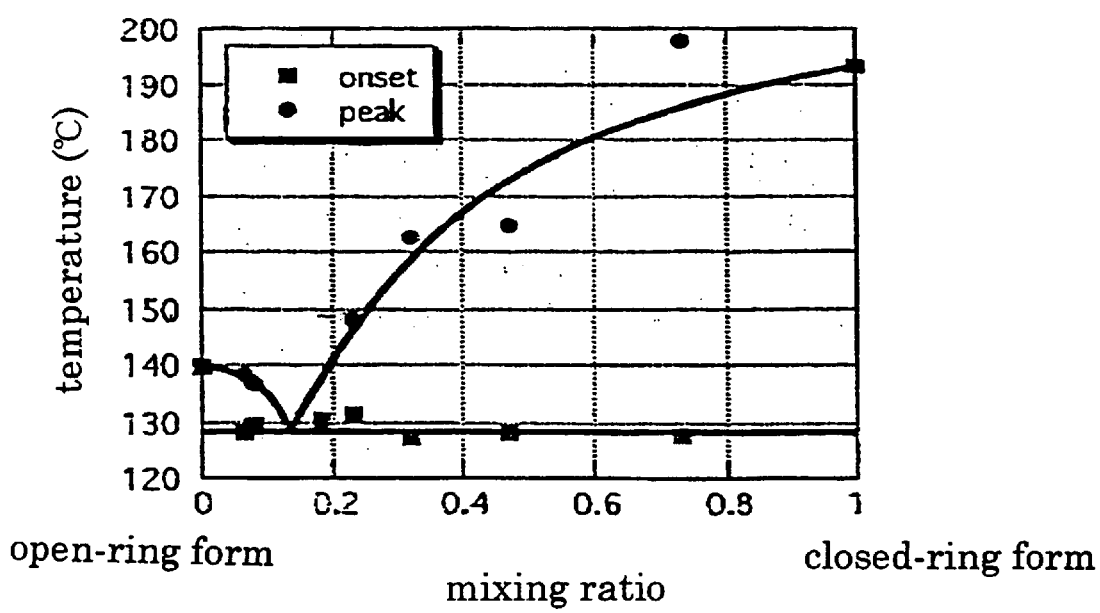

The melting point of the open-ring form (II-A) was 139° C. and that of the closed-ring form (II-B) was 193° C. The melting point of the closed-ring form (II-B) went down to 130° C. when it was irradiated with visible light having a wavelength of 500 nm or less. On the other hand, when the open-ring form (II-A) was irradiated with ultraviolet light having a wavelength of 350 to 400 nm, its melting point went up to 193° C. The behavior of the melting point to irradiation of light is illustrated in FIG. 1a. This behavior of the melting point was almost the same as that of the mixture of both crystals (II-A) and (II-B) as shown in FIG. 1b.

EXAMPLE 2

The closed-ring forms of the compound (III) were produced from a solution of compound (III) in hexane by irradiating the solution with ultraviolet rays having a wavelength of 313 nm. Among the resulted closed-ring forms, only the red one (III-B) was extracted by the column chromatography. The extracted closed-ring form was dissolved in hexane again, and then the closed-ring single crystal (III-B) was obtained from this solution by a solvent evaporation method.

When the closed-ring form (III-B) was irradiated with visible light having a wavelength of 450 nm or more at a room temperature for 30 minutes, its crystal melted. Furthermore, when the irradiation was continued on, the closed-ring form was recrystallized. It was thus apparent that the closed-ring form melted and recrystallized by irradiation of light.

It was apparent also from FIGS. 1a and 1b that the melting point of the compound varies depending on the mixing ratio of the open-ring form and the closed-ring form. The physical properties of the compound, such as the refractive index and the like, vary in cases that the compound is completely in liquid phase, completely in solid phase, or in solid-liquid mixed phase, and it is possible to take advantages of this feature of the compound to compose optical memory devices or display devices. For example, when the compound (II) which is composed fully of the open-ring form is irradiated with ultraviolet rays, while being kept at 135° C., so as to transform 15% of its component to the closed-ring form, the composition (mixture) becomes liquefied and changes in physical property, such as the refractive index and the permeability, from the original state. It is possible to take advantages of such changes of the physical properties of the compound to compose optical memory devices and display devices.

Industrial Applicability

Since the diheteroarylethene-based compound of the present invention reversibly changes in color with light irradiation and also changes in phase from the open-ring form in the crystalline state to the closed-ring form in the crystalline state, or from the closed-ring form in the crystalline state to the open-ring form in the crystalline state via the liquid state, the compound can be applicable to optical recording media, display panels, sensors, optical switch devices and the like, by taking advantages of its variations in color and also its changes in physical property, such as the refractive index and the permeability, with its changes in phase.

When the compound in the liquid state or in the solid-liquid mixed state is to be used for such applications as above, it may be sealed in a glass cell which is divided in many rooms in a grid-like arrangement or in a stripe-like arrangement, or sealed in glass cells which are independent of each other.

What is claimed is:

1. A photo-induced phase transition organic material composed of a diheteroarylethene compound within which photochromic reaction occurs in a crystalline state, said diheteroarylethene compound being expressed by a following general formula I:

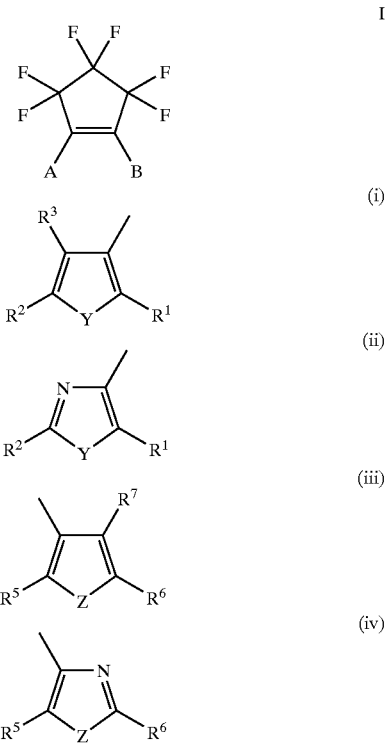

where substituents A and B are selected such that "A" expresses a substituent (i) or (ii), "R1" expresses an alkyl group, an alkoxyl group, a halogen atom, a trifluoromethyl group, a cyano group, or an aryl group which may have at least one substituent; "R2" and "R3" express a hydrogen atom, an alkyl group, an alkoxyl group, a halogen atom, a trifluoromethyl group, a cyano group, or an aryl group which may have at least one substituent, respectively, wherein "R2" and "R3" are independent of each other; or "R2" and "R3" are bonded to be a carbocyclic ring which may have at least one substituent, or a heterocyclic ring which may have at least one substituent; "Y" expresses —O—, —S—, or —NR$^4$— in which "R$^4$" expresses a hydrogen atom, an alkyl group which may have at least one substituent, an aryl group which may have at least one substituent, or a cycloalkyl group which may have at least one substituent; and "B"

expresses a substituent (iii) or (iv), "R5" expresses an alkyl group, an alkoxyl group, a halogen atom, or a trifluoromethyl group; "R6" and "R7" express a hydrogen atom, an alkyl group, an alkoxyl group, a halogen atom, a trifluoromethyl group, a cyano group, or an aryl group which may have at least one substituent, respectively, wherein "R6" and "R7" are independent of each other; or "R6" and "R7" are bonded to be carbocyclic ring which may have at least one substituent, or a heterocyclic ring which may have at least one substituent; "Z" expresses —O—, —S—, or —NR$^4$— in which "R$^4$" expresses a hydrogen atom, an alkyl group which may have at least one substituent, an aryl group which may have at least one substituent, or a cycloalkyl group which may have at least one substituent.

2. A photo-induced phase transition organic material as claimed in claim 1, wherein each of said substituents A and B is selected from the following substituents in which "R" expresses an alkyl group or a phenyl group:

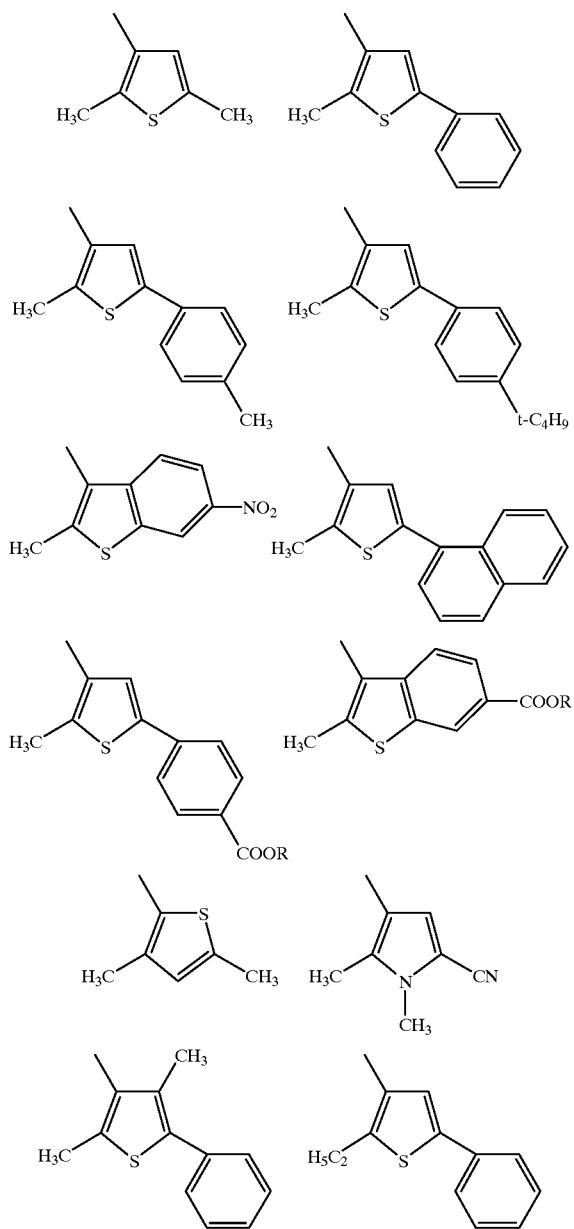

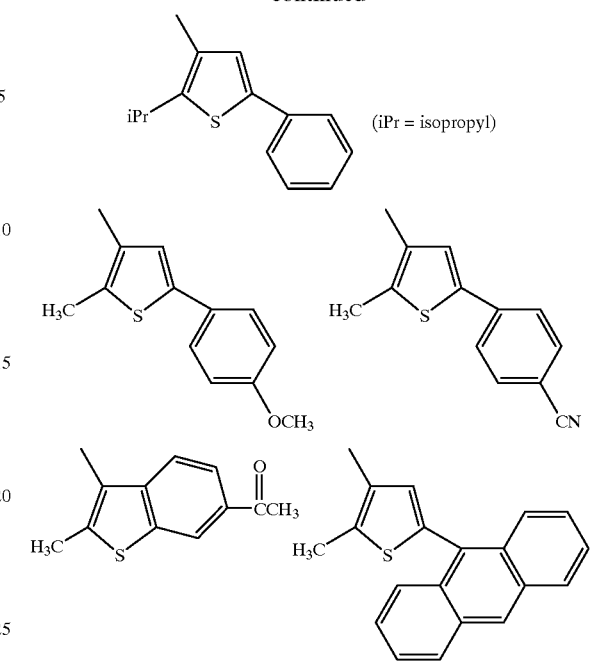

3. A photo-induced phase transition organic material as claimed in claim 2, wherein the diheteroarylethene compound is 1,2-bis (5-phenyl-2-methylthiophene-3-yl) perfluorocyclopentene as expressed by a following formula II:

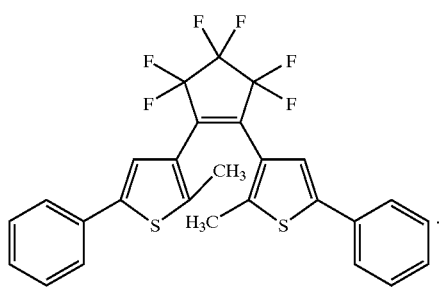

4. A photo-induced phase transition or organic material as claimed in claim 2, wherein the diheteroarylethene compound is 1,2-bis (2, 5-dimethylthiophene-3-yl) perfluorocyclopentene as expressed by a following formula III:

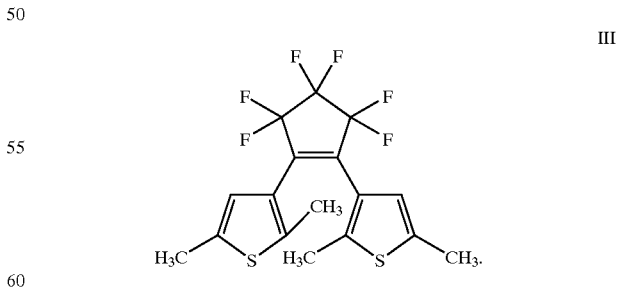

5. A photo-induced phase transition organic material as claimed in claim 1, wherein the diheteroarylethene compound is to be transferred in phase from an open-ring form to a closed-ring form with ultraviolet irradiation, and to be transferred in phase from the closed-ring form to the open-ring form with visible-light irradiation.

* * * * *